(12) United States Patent
Holtcamp et al.

(10) Patent No.: US 7,285,679 B2
(45) Date of Patent: Oct. 23, 2007

(54) OXIDATION OF ALKANES

(75) Inventors: Matthew W. Holtcamp, Huffman, TX (US); James C. Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/431,944

(22) Filed: May 10, 2006

(65) Prior Publication Data

US 2006/0293539 A1 Dec. 28, 2006

Related U.S. Application Data

(60) Provisional application No. 60/692,985, filed on Jun. 22, 2005.

(51) Int. Cl.
*C07C 27/10* (2006.01)
*C07C 53/00* (2006.01)

(52) U.S. Cl. ............................... 562/512.2

(58) Field of Classification Search ............ 562/512.2, 562/549
See application file for complete search history.

(56) References Cited

U.S. PATENT DOCUMENTS

| | | | |
|---|---|---|---|
| 5,198,580 A | 3/1993 | Bartek et al. | 562/542 |
| 5,380,933 A | 1/1995 | Ushikubo et al. | 562/549 |
| 5,789,333 A | 8/1998 | Angelici et al. | 502/113 |
| 6,060,421 A | 5/2000 | Karim et al. | 502/303 |
| 6,207,848 B1 | 3/2001 | Pressman | 558/274 |
| 6,407,031 B1 | 6/2002 | Chaturvedi et al. | 502/311 |
| 6,472,552 B1 | 10/2002 | Bogan, Jr. | 558/319 |
| 6,645,905 B2 | 11/2003 | Gaffney et al. | 502/311 |
| 6,646,158 B1 | 11/2003 | Khan et al. | 562/512.2 |
| 6,677,270 B2 | 1/2004 | Gaffney | 502/177 |
| 6,710,207 B2 | 3/2004 | Bogan, Jr. et al. | 562/549 |
| 6,740,620 B2 | 5/2004 | Bogan, Jr. et al. | 502/300 |
| 6,797,840 B2 | 9/2004 | Chaturvedi et al. | 562/542 |
| 2002/0123647 A1 | 9/2002 | Bogan, Jr. et al. | 562/545 |
| 2003/0017944 A1 | 1/2003 | Hinago et al. | 502/321 |
| 2004/0116737 A1 | 6/2004 | Gaffney et al. | 562/546 |

FOREIGN PATENT DOCUMENTS

| | | |
|---|---|---|
| EP | 0608838 | 4/1997 |
| EP | 1201636 | 5/2000 |
| JP | 145249/1988 | 6/1988 |
| JP | 170445/1991 | 7/1991 |
| JP | 1045643 | 2/1998 |

OTHER PUBLICATIONS

Nakagawa et al. Applied Catalysis A: "Partial Oxidation of Methane to Synthesis Gas over Iridium-nickel Bimetallic Catalyst" 1999 pp. 183-193.
Zhu B et al. Catalysis Today, "Effects of Reaction Conditions on the Selective Oxidation of Propane to Acrylic Acid on Mo-B-Te-Nb Oxides", vol. 93-95 2004 pp. 229-234.
Tang et al. Catalysis Letters, "Partial Oxidation of Methane to Synthesis gas over $\alpha$-$Al_2O_3$-Supported Bimetallic Pt-Co Catalysts" 1999 pp. 129-135.
G.S. Hill et al. Inoranic Syntheses, "Platinum (II) Complexes of Dimethyl Sulfide", vol. 32 1998 pp. 149-153.

*Primary Examiner*—Yvonne Eyler
*Assistant Examiner*—Jennifer Y Cho
(74) *Attorney, Agent, or Firm*—Catherine L. Bell

(57) ABSTRACT

Alkanes are oxidised to oxygenates such as carboxylic acids with molecular oxygen employing a two component catalyst system which uses a liganded heavy metal compound and a mixed metal oxide.

39 Claims, No Drawings

OXIDATION OF ALKANES

CROSS REFERENCE TO RELATED APPLICATIONS

This application claims priority to U.S. Provisional Patent Application No. 60/692,985, filed Jun. 22, 2005.

FIELD OF THE INVENTION

The present invention relates to the oxidation of alkanes to produce oxygen containing organic compounds such as alcohols, carbonyl containing compounds such as aldehydes and ketones and carboxylic acids. In particular, the invention is concerned with the oxidation of oxygen containing organic compounds such as alcohols, aldehydes, ketones, and carboxylic acids, specifically the oxidation of $C_1$ to $C_4$ alkanes, particularly methane, ethane and propane derived from natural gas.

BACKGROUND OF THE INVENTION

The availability of large quantities of natural gas has led to numerous proposals to upgrade the gas to more valuable chemicals including oxygen containing orgarnic compounds. The only commercial processes so far developed have required the sequential steps of catalytic dehydrogenation of the alkane to form an olefine followed by oxidation of the reactive olefinic site to produce the oxygenate. Other processes have been proposed for the direct oxidation of alkanes to oxygenates however these have low conversion and low selectivity and usually require high temperatures.

The two stage vapour phase oxidation of propylene for the production of acrylic acid is known to the art. However, there is no commercial process that exists based on propane oxidation to acrylic acid. The production of acrylic acid from propane would be more attractive because of the significant price difference between propane and propylene and the elimination of conversion steps.

There are few references reported in the literature relating to the production of acrylic acid from propane. U.S. Pat. No. 5,198,580 discloses a process for partial oxidation of propane to yield acrylic acid, propylene, acrolein, acetic acid and carbon oxides by the reaction of propane in admixture with a molecular oxygen-containing gas in a reaction zone with a catalyst containing $Bi_z$, $Mo_c$, $V_v$, $A_a$, $D_d$, $E_e$, $O_x$; where A is one or more of K, Na, Li, Cs and Tl; D is one or more of Fe, Ni, Co, ZXn, Ce and La; E is one or more of W, Nb, Sb, Sn, P, Cu, Pb, B, Mg, Ca and Sr, values for a, d and e are from 0 to 10, b is from 0.1 to 10, c is from 0.1 to 20, v is from 0.1 to 10, c:b is from 2:1 to 30:1 and v:b is from 1:5 to 8. The acrylic acid yield achieved using the bismuth molybdate type of catalyst is 4.5% at 19% conversion of propane at a pressure of 20 psig and a temperature of 400° C.

European Patent EP 0608838 A2 to Takashi et al discloses a method of producing an unsaturated carboxylic acid, mostly in the explosive regime of the propane, air and water mixture at 380° C. in the presence of a catalyst containing a mixed metal oxide of MoVTeXO, wherein X is at least one element selected from bismuth, cerium, indium, tantalum, tungsten, titanium, zirconium, chromium, manganese, iron, ruthenium, cobalt, rhodium, nickel, palladium, platinum and antimony, wherein the proportion of the respective essential components are based on the total amount of the essential components exclusive of oxygen and satisfy the following formulae: $0.25 < V_{mo} < 0.98$, $0.003 < V_v < 0.5$, $0.003 < V_x < 0.5$, wherein $V_{mo}$, V, $V_{Te}$ and $V_x$ are molar fractions of Mo, V, Te and X. Recently, Takashi et al disclosed in another JP Patent Number 1045643 (9845643-February 1998), the formation of acrylic acid and acrolein in the presence of $P_aMo_b$-$V_cW_dX_eO_n$ (X—Nb,Ta, Ti, Zr, Sb; if a=1 then b=1-18, c=0-4, d=0-4 and e=0.05-20) at 380° C. achieving a yield 0.9% to acrolein and 3.5% to acrylic acid at 12% propane conversion U.S. Pat. No. 6,646,158 suggests the use of a catalyst with a calcined composition of $MO_a$, $V_b$, $Ga_c$, $Pd_d$, $Nb_e$, $X_f$, wherein X=at least one element selected from the group consisting of La, Te, Ge, Zn, Si, In and W; a is 1; b is 0.01 to 0.9; c is >0 to 0.2; d is 0.000000001 to 0.2; e is >0 to 0.2; and f is >0 to 0.5 for the oxidation of propane to acrylic acid and acrolein. The numerical values of a, b, c, d, e and f represent the relative gram-atom ratios of the elements Mo, V, Ga, Pd, Nb and X respectively in the catalyst. The elements are preferably present in combination with oxygen in the form of various oxides.

The above referenced catalysts disclosed in the literature result in low yields of acrylic acid at relatively high temperatures and most produce propylene as one of the significant by-products. Propylene can be expensive and difficult to separate, especially in a recycling mode of operation.

Further examples of the mixed metal oxide component of the catalyst for the production of acrylic acid in one step by subjecting propane to a vapour phase catalytic oxidation reaction are a Mo—S-b-P—O type catalyst (European Patent No. 0010902), a CV—P—Te—O type catalyst (Journal of Catalysis, Col 101, p389 (1986)), a Bi—Mo—O type catalyst and a V—P—Te—O type catalyst (Japanese Unexamined Patent Publication No. 170445/1991). On the other hand, as an example of the catalyst for the production of methacrylic acid in one step by subjecting isobutene to a vapour phase catalytic oxidation reaction, a P—Mo—O type catalyst (Japanese Unexamined Patent Publication No. 145249/1988) is known.

However, each of the methods using such catalysts has a drawback such that the yield of the desired unsaturated carboxylic acid is not adequate or the reaction system is complex.

We have now developed a process that enables alkanes to be oxidised under less severe conditions and with a greater selectivity.

SUMMARY OF THE INVENTION

The present invention therefore provides a process for the oxidation of $C_1$ to $C_5$ alkanes comprising contacting the alkane with oxygen in the presence of a two component catalyst system said system comprising a first component which comprises a ligand co-ordinated heavy metal and a second component which comprises a mixed metal oxide.

The alkane should be contacted with the oxygen under oxidation conditions and the conditions that should be used will depend upon the nature of the alkane and the nature of the catalyst system that is used. The reaction may be performed in the gas phase or the liquid phase which may be solution or slurry. Gas phase is however preferred. Whatever the phase that is employed the use of the catalyst system according to this invention provides a degree of flexibility to enhance the production of the desired oxygen containing materials. Although the preferred oxidation conditions are specific to the alkane to be oxidised and the oxygen containing product to be produced the oxidation is typically performed with molecular oxygen generally provided as air and at a temperature in the range 150° C. to 450° C. more typically 200° C. to 400° C. preferably 200° C. to 350° C. more preferably 250° C. to 350° C. It is preferable to perform the reaction at elevated pressures, such as 1 to 10 atmospheres (101.3 to 1013 kPa), specifically 1 to 5 atmospheres (101.3 to 506.5 kPa).

Without being limited by theory, it is believed that the present invention and the derived benefits are accomplished by the combined effect that the ligand complexed heavy metal compound activates a carbon hydrogen bond in the alkane to render it susceptible to oxygen insertion and the mixed metal oxide catalyses the insertion of oxygen into the activated bond. The heavy metal and the ligand are chosen and the conditions selected according to the nature of the alkane and the degree of activation required. Once the carbon hydrogen bond has been activated the mixed metal oxide component of the catalyst system functions to insert one or more oxygen atoms into the activated site thus producing the desired oxygen containing organic compound. Choice of ligand, heavy metal, oxidation conditions and the nature of the mixed metal catalyst may all be varied to ensure that the desired product is obtained at improved conversions and selectivity.

The two component catalyst system used in the present invention may be a mixed catalyst system or may comprise two separate catalysts. Where two separate catalysts are used it is important that the alkane initially be exposed to the liganded heavy metal component to ensure activation of the carbon hydrogen bond so that it is susceptible to the insertion of oxygen during the second stage of the reaction. Such a staged reaction may be achieved in a single reactor with a stacked bed catalyst so that the alkane first passes through the bed of the liganded heavy metal component and then through the bed of the mixed metal oxide catalyst together with the oxygen source. In this embodiment the oxygen source may be fed into the reactor together with the alkane or alternatively some or all of the oxygen may be introduced into the reactor towards or at the end of the bed of the liganded heavy metal component.

Examples of heavy metals which may be used in the liganded heavy metal component of the catalyst system used in the present invention include palladium, platinum, osmium, rhenium, indium, rhodium, ruthenium and gold. Mixture of these metals may be used and the choice of metals will depend upon the alkane to be oxidised and the product it is desired to produce. Similarly the ligand that is used in the liganded heavy metal component of the catalyst system used in the present invention will depend upon the alkane to be oxidised and the product it is desired to produce. In alternate embodiments, the liganded metal is represented by the formula: R'LRLR" or the formula: R'LRLRLR", where each R is, independently, a linker organic/organometalloid moiety (preferably a hydrocarbyl group or a silyl group such as —$CH_2CH_2$, —$Si(CH_3)_2$—); each R' and R" are independently, hydrocarbyl: and may be different or the same hydrocarbyl group, each L is, independently, a heteroatom, preferably S, P, N, or O. Examples of suitable ligands include bidentate and tridentate heteroatom containing ligands. Ligands such as N,N,N,N-tetramethylethylenediamine, bipyridine, 2,6-bis[1-2,6-di-1-propylphenyl-imino) ethyl]pyridine $2,2^1$ $6^1,2^{11}$ terpyridine and 1, 2 bis (dimethyl phosphino) ethane may be employed. Halogen containing ligands and especially fluorine containing ligands may also be used.

The liganded heavy metal components of the catalyst system used in the present invention is preferably employed on a support. Preferred supports comprising alumina, silica, titania, zirconia and mixed metal oxides.

A preferred method for the preparation of the liganded heavy metal component of the present invention comprises combining the particular ligand with an appropriate heavy-metal species such that the ligand coordinates to the heavy-metal atom.

As with the liganded heavy metal component the preferred mixed metal oxide component employed in the two component catalyst systems used in the present invention will depend upon the alkane to be oxidised and the product that is to be produced. However, the mixed metal oxide may be selected from any of the mixed metal oxide catalysts that have previously been proposed for the oxidation of alkanes and examples of such compounds include the catalytic system which preferably comprises a calcined composition of $MO_a$, $V_b$, $Ga_c$, $Pd_d$, $Nb_e$, $X_f$, wherein X=at least one element selected from the group consisting of La, Te, Ge, Zn, Si, In and W; a is 1; b is 0.01 to 0.9; c is >0 to 0.2; d is 0.0000001 to 0.2; e is >0 to 0.2; and f is >0 to 0.5.

According to one embodiment of the invention the catalyst composition comprises $MO_a$, $V_b$, $Ga_c$, $Pd_d$, $Nb_e$, $X_f$, $O_y$, wherein y is a number determined by the valence requirements of the other elements in the catalyst composition. The catalyst of the invention can be used with or without a support. Suitable supports for the catalyst include alumina, silica, titania, zirconia, zeolites, silicon carbide, Mo carbide, molecular sieves and other micro/nonporous materials and mixtures thereof. When used with a support, the supported catalyst usually comprises from about 10 to 50% by weight of the catalyst composition with the remainder being the support material, in a preferred embodiment the supported catalyst usually comprises from about 5 to 80% by weight of the catalyst composition with the remainder being the support material, preferably 5 to 50%, and more preferably 10 to 40%.

Another aspect of the invention relates to methods of making the improved catalysts system and the individual components of the system. The choice of the compounds used as well as the specific procedures followed in preparing a catalyst can have a significant effect on the performance of a catalyst.

Preferably the mixed metal oxide component of the catalyst system is prepared from a solution of soluble compounds (salts, complexes or other compounds) of each of the metals. The solution is preferably an aqueous system having a pH of 1 to 10 and more preferably a pH of 1 to 7, at a temperature of from about 30 to about 100° C., preferably 35 to 80° C., and more preferably 40 to 60° C.

Generally a mixture of compounds containing the elements is prepared by dissolving sufficient quantities of soluble compounds and dispersing the insoluble compounds so as to provide the desired gram-atom ratios of the elements in the catalyst composition. The catalyst composition is then prepared by removing the water and/or other solvent from the mixture of the compounds in the solution system. The dried catalyst is calcined by heating to a temperature from about 250° C. to about 700° C. (preferably 300 to 650° C., more preferably 500-600° C., alternately from 250° C. to 450° C. in air or oxygen for a period of time from about one hour to about 16 hours, preferably 1 to 8 hours, more preferably 2 to 4 hours to produce the desired catalyst composition.

Molybdenum is one preferred metal and preferably the molybdenum is introduced into the solution in the form of ammonium salts such ammonium paramolybdate, or as organic acid salt of molybdenum such as acetates, oxalates, and glycolates. Other partially water soluble molybdenum compounds which may be used include molybdenum oxides, molybdic acid and chlorides of molybdenum.

Vanadium is another preferred metal and preferably the vanadium is introduced into the solution in the form of ammonium decavandate or as organic salts of vanadium such as acetates, oxalates and tartrates. Partially water soluble vanadium compounds such as vanadium oxides and sulphates of vanadium can also be used. To achieve a complete solubility a certain amount of oxalic or tartaric acid can be added.

When gallium is one of the metals preferably the gallium is introduced into the catalyst slurry in the form of salts of gallium such as oxide, chloride, nitrate and the like.

Similarly if palladium is one of the metals preferably the palladium is introduced into the catalyst slurry in the form of Pd on activated charcoal or alumina or as a solution of salts of palladium such as acetates, chlorides, nitrates and the like.

Other metals may be introduced into catalyst slurry in the form of salts of oxides, acetates, chlorides, nitrates or the like.

Preferably if niobium is used it is in the form of oxalates or hydrate oxides. Other sources of this metal in soluble form include compounds in which the metal is coordinated, bonded or complexed to a beta-diketone, carboxylic acid, an amine, an alcohol or an alkanolamine.

According to one preferred embodiment the mixed metal oxide component of catalyst is prepared by the following general procedure. Aqueous solutions of vanadium and molybdenum are prepared separately. The vanadium solution is mixed with the molybdenum solution at the desired temperature and pH. The remaining required components are slowly added to the combined solution. After mixing, the resultant gel is dried to incipient wetness with continuous stirring. After drying the resultant gel mixture at 120° C. for 16 hours, the resultant catalyst is heated to about 350° C. at a rate of 2° C. per minute and calcined at this temperature in air for 4 hours to produce the desired oxide composition.

Alternatively the two component catalyst systems may be prepared by reacting supported metal oxides such as the oxides of manganese, iron and cobalt with the liganded heavy-metal compounds.

The preferred mixed metal oxide to be used as a catalyst component of the present invention comprises Mo, V, Te, O and X wherein X is at least one element selected from the group consisting of niobium, tantalum, tungsten, titanium, alumium, zirconium, chromium, manganese, iron, ruthenium, cobalt, rhodium, nickel, palladium, platinum, antimony, bismuth, boron, indium, and cerium as essential components. Among the above elements for X, niobium, tantalum, tungsten and titanium are preferred. Particularly preferred is niobium.

The preferred proportions of the components based on the total amount of the components exclusive of oxygen are within the ranges defined by the following formulas; $0.25 < r_{Mo} < 0.98$; $0.003 < r_v < 0.5$; $0.003 < r_{Te} < 0.5$; $0.003 < r_x < 0.5$ wherein $r_{Mo}$, $r_v$, $r_{Te}$ and $r_x$ are molar fractions of Mo, V, Te and X, respectively based on the total amount of the essential components exclusive of oxygen. For example when the above mixed metal oxide is represented by the empirical formula $MO_aV_bTe_cX(1)_dX(2)_gO_g$ wherein X(1) and X(2) represent elements belong to the above element X, the respective molar fractions will be represented by the following formulas: $r_{Mo}=a/(a+b+c+d+e)$; $r_v=b/(a+b+c+d+e)$; $r_{Te}=c/(a+b+c+d+e)$; $r_x=(d+a)/(a+b+c+d+e)$.

As such proportions, the ranges represented by the following formulas are particularly preferred among the above molar fractions: $0.35 < r_{Mo} < 0.87$; $0.045 < r_v < 0.37$; $0.020 < r_{Te} < 0.27$; $0.005 < r_x < 0.35$ Further as the mixed metal oxide the one having a certain specific crystal structure is preferred. Specifically preferred is the one which exhibits the following five main diffraction peaks at specific diffraction angles 2θ in the x-ray diffraction pattern of the mixed metal oxide (as measured by using Cu—Kα ray as the X-ray source):

| X-ray lattice plane | | |
|---|---|---|
| Diffraction angle 2θ (±0.3) | Spacing medium (A) | Relative intensity |
| 22.1 | 4.02 | 100 |
| 28.2 | 3.16 | 20-150 |
| 36.2 | 2.48 | 5-60 |
| 45.2 | 2.00 | 2-40 |
| 50.0 | 1.82 | 2-40 |

The intensity of the X-ray diffraction peak may vary depending upon the measuring conditions of each crystal. However the relative intensity to the peak intensity at 22.1° being 100, is usually within the above ranges. Generally, the peak intensities at 20, 22.1° and 28.2° are distinctly observed. However, so long as the above face diffraction peaks are observable, the basic crystal structure is the same even if other peaks are observed in addition to the five diffraction peaks, and such a structure is useful for the present invention.

The mixed metal oxide can be prepared by the following method. For example, when a mixed metal oxide of the formula $Mo_aV_bTe_cNb_xO_n$, is to be prepared, an aqueous solution of telluric acid, an aqueous solution of ammonium niobium oxalate and a solution or slurry of ammonium paramolybdate are sequentially added to an aqueous solution containing a predetermined amount of ammonium metavanadate, so that the atomic ratio of the respective metal elements would be in the prescribed proportions, the mixture is then dried by e.g. evaporation to dryness, spray drying or vacuum drying, and finally the remaining dried product is calcined usually at a temperature of from 350° to 700° C. preferably from 400° to 650° C. usually for form 0.5 to 30 hours preferably from 1 to 10 hours, to obtain the desired mixed metal oxide.

The above calcinations treatment can be conducted in an oxygen atmosphere, but it is preferred to conduct the calcinations treatment substantially in the absence of oxygen. Specifically the treatment is carried out in an inert gas atmosphere of e.g. nitrogen, argon or helium, or in vacuo.

The starting materials for the above mixed metal oxide are not limited to those described above. For example, a wide range of materials including oxides such as $MoO_3$, $V_2O_5$, $V_2O_3$, $TeO_2$ and $Nb_2O_5$, halides or oxyhalides such as $MoCl_5$, $VCl_4$, $VOCl_3$ and $NbCl_5$, alkoxides such as $Mo(OC_2H_5)_5$, $Nb(OC_2H_5)$, $VO(OC_2H_5)_3$ and acetylacetone molybdenyl and organometallic compounds may be used.

A mixed metal oxide thus obtained, exhibits excellent catalytic activity. However it can be converted to a catalyst having higher activity by grinding such a mixed metal oxide.

There is no particular restriction as to the grinding method, and conventional methods may be employed. As a dry grinding method, a method of using a gas stream grinder may, for example, be mentioned wherein coarse particles are permitted to -collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the mixed metal oxide, a conventional method of using a rotary cylinder-type medium mill or a medium stirring type mill may be mentioned. The rotary cylinder type medium mill is a wet mill of the type wherein a container for the object to be ground is rotated and it includes for example, a ball mill and a rod mill. The medium-stirring type mill is a wet mill of the type wherein the object to be ground, contained in a container is stirred by a stirring apparatus and it includes for example a rotary screw type mill and a rotary disk type mill.

The conditions for grinding may suitably be set to meet the nature of the above mentioned mixed metal oxide, the viscosity, the concentration etc of the solvent used in the case of the wet grinding, or the optimum conditions of the grinding apparatus. However it is preferred that grinding is conducted until the average particle size of the ground catalyst precursor would be at most 20 μm, more preferably at most 5 μm. Improvement in the catalytic performance can be observed by grinding to such an extent.

Further in some cases it is possible to further improve the catalytic activities by adding a solvent to the ground catalyst precursor to form, a solution or slurry, following by drying again. There is no particular restriction as to the concentration of the solution or slurry and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by spray drying method. Further similar drying may be conducted also in the case where wet grinding is conducted.

The oxide obtained by the above mentioned method may be used as the final mixed metal oxide component of the catalyst system of the present invention, although it may further be subjected to heat treatment usually at a temperature of from 200° to 700° C., preferably 300 to 650° C., more preferably 500 to 600° C. for from 0.1 to 10 hours.

The mixed metal oxide thus obtained may be used by itself as a solid catalyst, component of the present invention alternatively it may be formed into a catalyst together with a suitable carrier such as silica, alumina, titania, aluminosilicate, diatomaceous earth or zirconia. Further it may be moulded into a suitable shape and particle size depending upon the scale or system of the reactor.

The relative proportions of the two components of the catalyst system used in the present invention that should be used depends upon the alkane to be oxidised and the product it is desired to produce. However we prefer to use the liganded heavy metal in amounts such that a finished supported catalyst contains less than 3 wt % heavy metal in the finished catalyst and greater than 0.0005 wt %, preferably less than 2 wt %, preferably less than 1 wt%, more preferably less than 7 wt %.

Where propane is the raw material the source of the propane can be a gas stream which contains at least three volume percent of propane or a mixture of propylene and propane. The gas stream can also contain some amounts of the $C_2$ or $C_4$ alkanes, preferably less than thirty volume percent of each. The gas stream can also contain major amounts, more than five volume percent of diluents such as nitrogen, argon, carbon dioxide and water in the form of steam. In carrying out the process with propane as the raw material the reaction mixture generally contains one mole of propane, 0.01 to 2.0 moles of molecular oxygen either as pure oxygen or in the form of air, and zero to 4.0 moles of water in the form of steam.

Molecular oxygen sources for the feed include purified oxygen, air and oxygen-enriched air, depending on the economics of separation and the hydrocarbon conversion achieved. The ratio of alkane to oxygen varies with the desired conversion and the selectivity of the catalyst, but generally in the range of 1/5-5/1.

The oxygen concentration in the feed gas mixture can vary widely, from 0.1 to 50% or higher of the feed mixture by applying proper measures to avoid explosion problems. Air is the preferred source of oxygen in the feed. The amount of oxygen present may be a stoichiometric amount, or lower, in relation to the hydrocarbons in the feed.

The reaction can also be affected in the presence of diluents such as argon, nitrogen or steam. The ratio of propane to diluents can be in the range of 1/5-1/1.

Water vapour or steam may be used as a reaction diluent and as a heat moderator for the reaction. It also can act as a desorption accelerator of the reaction product in the vapour phase oxidation reaction. Other gasses may be used as reaction diluents or heat moderators such as helium, nitrogen and carbon dioxide.

The gaseous components of the reaction mixture preferably include alkane, oxygen or oxygen and diluents and these components are preferably uniformly admixed prior to being introduced into the reaction zone. The components may be preheated, individually or after being admixed, prior to being introduced into the reaction zone which preferably has a temperature of from about 50° C. to about 450° C.

The reaction zone for the oxidations of the invention preferably has a pressure of from 1 to 50 bar preferably from 1 to 30 bar, a temperature of from about 150° C. to about 450° C., preferably from 150° C. to 300° C. more preferably 150° C. to 250° C.; a contact time between the reaction mixture and the catalyst of from about 0.01 second to 100 seconds, preferably from 0.1 second to 10 seconds, and/or space hourly velocity of from about 50 to about 50,000 $h^{-1}$, preferably from 100 to 10,000 $h^{-1}$ and most preferably from 200 to 3,000 $h^{-1}$.

The contact time is defined as the ratio between the apparent volume of the catalyst bed and the volume of the gaseous reaction mixture feed to the catalyst bed under the given reaction conditions in a unit of time.

The space velocity is calculated by determining the total reactor outlet gas equivalent in litres of the total effluent evolved over a period of one hour divided by the litres of catalyst in the reactor. This room temperature volume is converted to the volume at 0° C. at 1 bar.

The reaction pressure may be initially provided by the feed of the gaseous reactant and diluent and after the reaction has commenced, may be maintained by the use of a suitable back pressure controller placed on the reactor outlet stream.

The process may be carried out in a single stage with all the oxygen and reactants being supplied as a single feed with non-reacted initial reactants being recycled. However multiple stage addition of oxygen or hydrocarbon to the reactor can be used and/or recycling of un-reacted gases with purge mode can be applied to improve the overall productivity and/or yield of the desired products. Alternatively the process may be carried out using a staged reaction such as previously described.

The liquid products of the reaction can be separated from the unreacted feed hydrocarbons by condensation or scrubbing, usually by water or dilute acid.

The catalyst systems previously described may be used for oxidizing $C_1$-$C_5$ alkanes, preferably $C_2$-$C_4$ alkanes such as acrolein, ethane, propane and butane, to produce corresponding oxygenated products such as acetic, acrylic and methacrylic acids, and, e.g. for oxidizing n/iso $C_4$ and $C_5$ in the vapour phase with molecular oxygen to produce the corresponding alpha-beta unsaturated carboxylic acids. The invention is particularly useful for the oxidation of propane to acrylic acid and acrolein.

The ability to vary the catalyst system within the concept of the use of a dual purpose catalyst system in which one component imparts the desired degree of activation to the carbon hydrogen bond of the alkane to render it susceptible to oxygen insertion and another compound catalyses the insertion of the oxygen allows the catalyst to be tailored to the particular oxidation reaction and provides an increased degree of flexibility. This in turn allows the yield and the selectivity of the oxidation reaction to be increased. Furthermore the use of the catalyst component that activates the carbon hydrogen bond of the alkane can allow the oxygen insertion reaction to be accomplished under milder conditions (of temperature and pressure) than has hitherto been possible. A further benefit is that the direct oxidation reaction removes only a single hydrogen atom from the alkane thus producing less water than the previous commercial oxidation reactions which proceed through the olefin intermediate requiring the removal of at least two hydrogen atoms and the formation and removal of twice the amount of water.

The catalyst system of the present invention is illustrated by reference to the following Examples.

$(\mu_2$-$Me_2S)_2(Pt(CH_3)_2)_2$ was prepared as described by Puddephatt et al. in Inorg. Syn. 1998, 32, 149-153.

V(Mo)(Nb)TeO was prepared as described in Zhu et al in Catalysis Today 93-95 (2004) 229-234 as follows: To nine hundred grams of distilled water the following salts were added in order with stirring:

ammonium metavanadate—$NH_4VO_3$ 10 grams ammonium heptamolybdate tetrahydrate—$(NH_4)_6Mo_7O_{24} \cdot 24H_2O$ 52 grams telluric acid—$Te(OH)_6$ 15.5 grams niobium oxalate—$Nb(HC_2O_4)_5$ 18.6 grams This solution was stirred for one hour. The solution was then placed in a rotoevaporator and the mixture was evacuated to dryness at 50° C. A portion of the dried material was then calcined in nitrogen at 600° C. for 2 hours. The molar ratio of the calcined material was $V_{0.16}Mo_{0.63}Nb_{0.084}Te_{0.125}$

EXAMPLE 1

$[((CH_3CH_2)S(CH_2)_2)_2NH]Pt(CH_3)_2$ was prepared by combining 0.5 grams of $(\mu2$-$Me_2S)_2(Pt(CH_3)_2)_2$ with 0.336 grams of $((CH_3CH_2)S(CH_2)_2)_2NH$ in toluelen(30 mls). The reaction was stirred for at least sixteen hours. The solvent was removed by vacuum yielding an oil.

$[((CH_3CH_2)S(CH_2)_2)_2NH]Pt(CH_3)_2N(Mo)(Nb)TeO$ was then prepared by combining 0.061 grams of the $[((CH_3CH_2)S(CH_2)_2)_2NH]Pt(CH_3)_2$ with 1.0 grams of V(Mo)(Nb)TeO as prepared above and slurried in toluene. The slurry was allowed to sit at least sixteen hours at room temperature. The solids were then filtered and dried under vacuum. After pelletization a 0.5 gram sample diluted with 1.0 grams of silicon carbide was subjected to propane and oxygen at 380° C.: 0.42 g, 9.8 conv, 11.6% sel to propylene, 0.5% sel to acetic acid, 0.5% sel to acrylic acid.

EXAMPLE 2

$[((CH_3CH_2)S(CH_2)_2)_2NH]Pt(CH_3)_2N(Mo)(Nb)TeO$ (100° C.) was prepared by repeating Example 1 except the slurry in toluene was heated to 100° C. for at least 16 hours.

EXAMPLE 3

$(C_8H_6N_4)Pt(CH_3)_2$ was prepared by combining 0.5 grams of $(P_2$—$Me_2S)_2(Pt(CH_3)_2)_2$ with 0.28 grams of $C_8H_6N_4$, bipyrimidine, in toluene (25 mls). The reaction was stirred for at least sixteen hours. The resulting dark red slurry was filtered and the solids were dried under vacuum, the yield was 0.5 grams.

$(C_8H_6N_4)Pt(CH_3)_2N(Mo)(Nb)TeO$ was then prepared by combining 0.061 grams $(C_8H_6N_4)Pt(CH_3)_2$ was combined with 1.0 grams of V(Mo)(Nb)TeO prepared as previously described and the mixture was slurried in toluene. The slurry was allowed to sit at least sixteen hours at room temperature. The solids were filtered and dried under vacuum.

All the catalysts were pelletized and crushed to 60/100 mesh particles and then diluted with 10 g of silicon carbide inert. The catalyst was tested with a gaseous feed consisting of 14% propane, 7% oxygen, 79% helium. The feed rate was 50 cc/min while the reactor pressure was 50 psig (0.35 MPa). The steam rate was controlled at 0.0.01 g/min.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

The invention claimed is:

1. A process for the oxidation of $C_1$ to $C_5$ alkanes comprising contacting the alkane with oxygen in the presence of a two component catalyst system said system comprising a first component which comprises a ligand co-ordinated heavy metal, where the heavy metal is selected from palladium, platinum, osmium, rhenium, indium, rhodium, ruthenium and gold and mixtures thereof, and the ligand is selected from N,N,N,N-tetramethylethylenediamine, bipyridine, 2,6-bis[1-2,6-di-I-propylphenyl-imino)ethyl]pyridine, $2,2^16^1,2^{11}$ terpyridine and 1,2 bis (dimethyl phosphino) ethane and mixtures thereof; and a second component which comprises a mixed metal oxide, where the mixed metal oxide comprises a calcined composition of $Mo^a$, $V_b$, $Ga_c$, $Pd_d$, $Nb_e$, and $X_f$, wherein X=at least one element selected from the group consisting of La, Te, Ge, Zn, Si, In and W; a is 1; b is 0.01 to 0.9; c is >0 to 0.2; d is 0.0000001 to 0.2; e is >0 to 0.2; and f is >0 to 0.5.

2. A process according to claim 1 in which the reaction is performed in the gas phase.

3. A process according to claim 1 in which the reaction is performed in the liquid phase which may be solution or slurry.

4. A process according to claim 1 in which the oxygen containing product is molecular oxygen provided as air.

5. A process according to claim 1 in which the reaction is performed at a temperature in the range 150° C. to 450° C.

6. A process according claim 1 in which the two component catalyst system used in the present invention is a mixed catalyst system.

7. A process according to claim 1 in which the catalyst system comprises two separate catalysts and the alkane is initially exposed to die liganded heavy metal component.

8. A process according to claim 1 performed in a single reactor with a stacked bed catalyst wherein the alkane first passes through the bed of the liganded heavy metal component and then through the bed of the mixed metal oxide catalyst together with the oxygen source.

9. A process according to claim 8 in which the oxygen source is fed into the reactor together with the alkane.

10. A process according to claim 8 in which some or all of the oxygen is introduced into the reactor towards or at the end of the bed or the liganded heavy metal component.

11. A process according to claim 1 in which the ligand is selected from bidentate and tridentate heteroatom containing ligands.

12. A process according to claim 1 in which the tiganded heavy metal components of the catalyst system is employed on a support.

13. A process according to claim 12 in which the support is selected from alumina, silica, titania, zirconia and mixed metal oxides.

14. A process according to claim 1 in which the two component catalyst system is prepared by reacting supported metal oxides selected from the aroup consisting of oxides of manganese, iron and cobalt with the liganded heavy-metal compounds.

15. A process according to claim 1 in which the mixed metal oxide exhibits the following five main diffraction peaks at specific diffraction angles 2θ in the x-ray diffraction pattern of the mixed metal oxide (as measured by using Cu-Kα ray as the X-ray source).

| X-ray lattice plane | | |
|---|---|---|
| Diffraction angle 2θ (±0.3) | Spacing medium (A) | Relative intensity |
| 22.1 | 4.02 | 100 |
| 28.2 | 3.16 | 20-150 |
| 36.2 | 2.48 | 5-60 |
| 45.2 | 2.00 | 2-40 |
| 50.0 | 1.82 | 2-40. |

16. A process according to claim 1 in which the liganded heavy metal is present in an amount such that the finished supported catalyst contains greater than 0.005 wt % and less than 2 wt % heavy metal in the finished catalyst.

17. A process according to claim 1 in which the alkane is propane.

18. A process according to claim 17 in which the soPrce of the propane is a gas stream which contains at least three volume percent of propane or a mixture of propylene and propane and less than thirty vohune percent of $C_1$ or $C_5$ alkanes.

19. A process according to claim 17 in which the gas stream also contains more than five volume percent of diluents selected from nitrogen, argon, carbon dioxide and water in the form of steam and mixtures thereof.

20. A process according to claim 17 in which the reaction mixture contains one mole of propane, 0.01 to 2.0 moles of molecular oxygen either as pure oxygen or in the form of air, and zero to 4.0 moles of water in the fonn of steam.

21. A process according to claim 1 in which the oxygen source comprises purified oxygen, air or oxygen-enriched air.

22. A process according to claim 1 in which the ratio of alicane to oxygen is in the range of 1/5 to 5/1.

23. A process according to claim 1 in which the reaction is affected in the presence of one or more diluents selected from the group consisting of argon, nitrogen and steam.

24. A process according to claim 23 in which the ratio of propane to diluents is in the range of 1/5-1/1.

25. A process according to claim 1 in which the water vapour or steam is used as a reaction diluent and as a heat moderator for the reaction.

26. A process according to claim 1 in which the gaseous components of the reaction mixture are uniformly admixed prior to being introduced into the reaction zone.

27. A process according to claim 1 in which the gaseous components are preheated individually or after being admixed, prior to being introduced into the reaction zone.

28. A process according to claim 1 in which the reaction zone has a pressure of from 1 to 50 bar, a temperature of from about 150° C. to about 450° C., and the contact time between the reaction mixture and the catalyst is from about 0.01 second to 100 seconds, at a space hourly velocity of from about 50 to about 50,000 $h^{-1}$.

29. A process according to claim 1 in which the process is carried out in a single stage with all the oxygen and reactants being supplied as a single feed with non-reacted initial reactants being recycled.

30. A process according to claim 1 in which a multiple stage addition of oxygen or hydrocarbon to the reactor is used.

31. A process according to claim 1 in which recycling of un-reacted gases with purge mode is applied.

32. A process according to claim 1 comprising oxidizing $C_1$-$C_5$ alkanes to produce carboxylic acids.

33. A process for the oxidation of $C_1$ to $C_5$ alkanes comprising contacting the alkane with oxygen in the presence of a two component catalyst system said system comprising a first component which comprises a ligand co-ordinated heavy metal, where the heavy metal is selected from palladium, platinum, osmium, rhenium, indium, rhodium, ruthenium and gold and mixtures thereof, and the ligand is selected from N,N,N,N-tetramethylethylenediamine, bipyridine, 2,6-bis[1-2,6-di-I-propylphenyl-imino)ethyl]pyridine, $2,2^16^1,2^{11}$ terpyridine and 1,2 bis (dimethyl phosphino) ethane and mixtures thereof; and a second component which comprises a mixed metal oxide, where the mixed metal oxide comprises Mo, V, Te, O and X wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium, and cerium.

34. A process according to claim 33 in which the mixed metal oxide exhibits the following five main diffraction peaks at specific diffraction angles 2θ in the x-ray diffraction pattern of the i-nixed metal oxide (as measured by using Cu-Kα ray as the X-ray source).

| X-ray lattice plane | | |
|---|---|---|
| Diffraction angle 2θ (±0.3) | Spacing medium (A) | Relative intensity |
| 22.1 | 4.02 | 100 |
| 28.2 | 3.16 | 20-150 |
| 36.2 | 2.48 | 5-60 |
| 45.2 | 2.00 | 2-40 |
| 50.0 | 1.82 | 2-40. |

35. A process according to claim 33 in which the reaction zone has a pressure of from 1 to 50 bar, a temperature of from about 150° C. to about 450° C., and the contact time between the reaction mixture and the catalyst is from about 0.01 second to 100 seconds, at a space hourly velocity of from about 50 to about 50,000 $h^{-1}$.

36. A process according to claim 33 performed in a single reactor with a stacked bed catalyst wherein the alkane first passes through the bed of the liganded heavy metal component and then through the bed of the mixed metal oxide catalyst together with the oxygen source.

37. A process according to claim 36 in which the oxygen source is fed into the reactor together with the alkane.

38. A process according to claim 36 in which some or all of the oxygen is introduced into the reactor towards or at the end of the bed of die liganded heavy metal component.

39. A process according to claim 33 in which die alkane is propane.

* * * * *